United States Patent [19]

Glenn

[11] 4,246,791
[45] Jan. 27, 1981

[54] ULTRASONIC IMAGING APPARATUS

[75] Inventor: William E. Glenn, Ft. Lauderdale, Fla.

[73] Assignee: New York Institute of Technology, Old Westbury, N.Y.

[21] Appl. No.: 890,378

[22] Filed: Mar. 27, 1978

[51] Int. Cl.³ .............................................. G01N 29/04
[52] U.S. Cl. ........................................ 73/620; 128/660
[58] Field of Search ........... 128/2 V, 205 Z, 660–663; 310/334–337; 340/8 R, 8 FT; 73/618–626, 642

[56] References Cited

U.S. PATENT DOCUMENTS

| | | | |
|---|---|---|---|
| 3,159,023 | 12/1964 | Steinbrecher | 128/2 V |
| 3,550,438 | 12/1970 | Kapluszak | 73/642 X |
| 3,936,791 | 2/1976 | Kossoff | 128/2 V |
| 4,047,520 | 9/1977 | Soldner et al. | 128/2 V |
| 4,084,582 | 4/1978 | Nigam | 73/620 X |
| 4,110,723 | 8/1978 | Hetz et al. | 73/620 |
| 4,137,777 | 2/1979 | Haverl et al. | 73/626 X |

OTHER PUBLICATIONS

Mountford, R. A. et al., "Semi-Automatic Transducer Movement for Ultrasonic Compound B Scanning", MBE, vol. 12, No. 6, Mar. 1974, pp. 227–232.
Fesenko, A. D. et al., "UTS Inspection of High-Tensile Tubes", *Industrial Labs*, Plenum Publ., NY, 1971, pp. 812–813.

*Primary Examiner*—Kyle L. Howell
*Assistant Examiner*—Francis J. Jaworski
*Attorney, Agent, or Firm*—Martin Novack

[57] ABSTRACT

A portable ultrasonic scanning module is disclosed which includes a fluid-tight enclosure having a window at about the front thereof and a reflective scanner at about the rear thereof and generally facing the window. A transducer is mounted in the enclosure frontwardly of the reflective scanner with the ultrasound-emitting face of the transducer generally facing the reflective scanner and being oriented with respect to the reflective scanner at a relatively acute angle such that the beam effectively "doubles-back" past itself during its excursion through the scanning module.

90 Claims, 5 Drawing Figures

4,246,791

ULTRASONIC IMAGING APPARATUS

BACKGROUND OF THE INVENTION

This invention relates to ultrasonic systems and, more particularly, to apparatus for imaging sections of a body by transmitting ultrasonic energy into the body and determining the characteristics of the ultrasonic energy reflected therefrom. The subject matter of this application is related to subject matter disclosed in my copending U.S. Patent Application Ser. No. 890,377 entitled "Apparatus for Ultrasonically Imaging A Body", filed of even date herewith and assigned to the same assignee as the present application.

In recent years ultrasonic techniques have become more prevalent in clinical diagnosis. Such techniques have been utilized for some time in the field of such obstetrics, neurology and cardiology, and are becoming increasingly important in the visualization of a number of different body portions, for example the scanning of breasts to detect tumors.

Various fundamental factors have given rise to the increased use of ultrasonic techniques. Ultrasound differs from other forms of radiation in its interaction with living systems in that it has the nature of a mechanical wave. Accordingly, information is available from its use which is of a different nature than that obtained by other methods and it is found to be complementary to other diagnostic methods, such as those employing X-rays. Also, the risk of tissue damage using ultrasound appears to be much less than the apparent risk associated with ionizing radiations such as X-rays.

The majority of diagnostic techniques using ultrasound are based on the pulse-echo method wherein pulses of ultrasonic energy are periodically generated by a suitable piezoelectric transducer such as a lead zirconate-titanate ceramic. Each short pulse of ultrasonic energy is focused to a narrow beam which is transmitted into the patient's body wherein it eventually encounters interfaces between various different structures of the body. When there is a characteristic impedence mismatch at an interface, a portion of the ultrasonic energy is reflected at the boundary back toward the transducer. After generation of the pulse, the transducer operates in a "listening" mode wherein it converts received reflected energy or "echoes" from the body back into electrical signals. The time of arrival of these echoes depends on the ranges of the interfaces encountered and the propagation velocity of the ultrasound. Also, the amplitude of the echo is indicative of the reflection properties of the interface and, accordingly, of the nature of the characteristic structures forming the interface.

There are various ways in which the information in the received echoes can be usefully presented. In one common technique, the electrical signal representative of detected echoes are amplified and applied to the vertical deflection plates of a cathode ray display. The output of a time-base generator is applied to the horizontal deflection plates. Continuous repetition of the pulse/echo process in synchronism with the time-base signals produces a continuous display, called an "A-scan", in which time is proportional to range, and deflections in the vertical direction represent the presence of interfaces. The height of these vertical deflections is representative of echo strength.

Another common form of display is the so-called "B-scan" wherein the echo information is of a form more similar to conventional television display; i.e., the received echo signals are utilized to modulate the brightness of the display at each point scanned. This type of display is found especially useful when the ultrasonic energy is scanned transverse the body so that individual "ranging" information yields individual scan lines on the display, and successive transverse portions are utilized to obtain successive scan lines on the display. The two-dimensional B-scan technique yields a cross-sectional picture in the plane of the scan, and the resultant display can be viewed directly or recorded photographically or on magnetic tape.

While successes have been achieved in the field of ultrasonic imaging, there are a number of problems which need to be overcome in obtaining high quality ultrasonic images in a convenient, reliable and cost-effective manner. Regarding problems which have been partially overcome, it is known, for example, that ultrasound is almost totally reflected at interfaces with gas. This has led to the use of coupling through a fluid such as water or the use of a direct-contact type of transducer. The latter technique may give rise to problems when attempting to image structures such as arteries which may be only a few millimeters below the skin surface, the contact imaging causing aberrations in the near field of the transducer. Coupling through a fluid offers advantage over direct-contact in this respect, but leads to various design problems and cumbersome generally non-portable structures which are inconvenient to use, especially when attempting to register them accurately on a patient. Some techniques involve immersing the patient in water or obtaining appropriate contact of the body part with a bulky water tank wall.

The need to scan the ultrasonic beam in two dimensions gives rise to problems of bulkiness and difficulty of handling in the scanning unit. In the co-pending Application Ser. No. 665,898, now U.S. Pat. No. 4,084,582 assigned to the same assignee as the present invention, there is disclosed a type of apparatus which provides improved convenience as compared to most water coupled imaging techniques. The apparatus disclosed therein has a console which typically includes a timing signal generator, energizing and receiving circuitry, and a display/recorder for displaying and/or recording image-representative electronic signals. A portable scanning module, suitable for being hand held, has a fluid-tight enclosure having a scanning window formed of a flexible material. A transducer in the portable scanning module converts energy from the energizing circuitry to ultrasonic energy and also converts received ultrasound echoes back into electrical signals which are coupled to the receiver circuitry. A focusing lens is coupled to the transducer, and a fluid, such as water, fills the portable scanning module in the region between the focusing lens and the scanning window. A reflective scanner is disposed in the fluid, and the driving motor, energized in synchronism with the timing signals, drives the reflective scanner in periodic fashion.

A scanning module of the type disclosed in the referenced co-pending application is advantageous in that it is portable and relatively light and easy to handle as compared to other prior art scanners known to applicant. However, it would be most advantageous to develop a portable ultrasonic scanning module which is smaller, lighter, easier to handle and use, requires less mechanical drive power, and is otherwise operationally advantageous as compared to prior art scanners.

It is an object of the present invention to improve upon existing ultrasonic scanners, and especially ultrasonic scanners of the portable hand-held type.

SUMMARY OF THE INVENTION

The present invention is applicable to an ultrasonic apparatus for imaging sections of a body by transmitting ultrasonic energy into the body and determining the characteristics of the ultrasonic energy reflected therefrom. Such an apparatus typically includes timing means for generating timing signals, energizing/receiving means alternately operative in response to the timing signals, and display/record means, synchronized by the timing signals, for displaying and/or recording image-representative electronic signals from the energizing/receiving means. These elements are typically, although not necessary, located in a console.

In accordance with the invention there is provided a portable scanning module, suitable for being hand held, which comprises fluid-tight enclosure having a window at about the front thereof and a reflective scanner at about the rear thereof and substantially facing the window. A transducer is provided for converting energy from the energizing/receiving means to a beam of ultrasonic energy and for converting reflected ultrasonic energy to electrical signals. The transducer is mounted in the enclosure frontwardly of the reflective scanner with an ultrasound-emitting face of the transducer facing the reflective scanner and being oriented with respect to the reflective scanner such that an ultrasound beam reflected by the reflective scanner as between the transducer and the window subtends an angle at the reflective scanner of less than about forty-five degrees. Fluid means, typically although not necessarily water, fills the enclosure. Finally, driving means, synchronized with the timing signals, are provided for moving the scanning means in periodic fashion so as to effect a scan of the ultrasound beam through the window.

In the preferred embodiment of the invention, the angle of the ultrasound beam subtended at the reflective scanner is about thirty degrees. Generally, if the ultrasound impinges on a surface at an angle too close to the normal (i.e., at an angle less than the "critical angle"), a substantial portion of the ultrasound energy will pass through the surface. In order to have virtually all of the ultrasound energy which impinges upon the scanner be reflected therefrom, it is necessary to have the ultrasound impinge upon the reflective scanner at an angle which is at least as great as the critical angle. Applicant has found that sapphire (aluminum oxide) on the surface of the reflective scanner gives rise to a critical angle of about fourteen degrees and allows utilization of a transducer position which makes better use of the volume of fluid in the enclosure and leads to a smaller, lighter, and easier to handle scanning module. Beryllium also results in a small critical angle, but its toxicity renders it less desirable to work with. A further alternative is to employ a reflective scanner having a trapped gas layer, as disclosed in copending U.S. Application Ser. No. 665,898, assigned to the same assignee of the present application. As described therein, the liquid/gas interface at the reflector surface insures total reflection regardless of the beam arrival angle. As will become clear, the relatively acute angle (with respect to the normal) at which the beam impinges on the reflective scanner means that the beam can be made to effectively "double back" past itself during its excursion through the scanning module. Various considerations, including minimizing artifacts which might otherwise be produced by reflection of ultrasound from the skin and then off the transducer, dictate a certain minimum distance from the transducer to the object being scanned. Using the present invention, distance considerations are met while still employing a relatively small and compact scanning module.

In the present embodiment of the invention, the transducer is elliptical and elongated along the direction of scanning of the beam. This results in an effective elongation of the scanning spot in a direction perpendicular to the direction of scan, the details of this feature being further described in my copending U.S. Application Ser. No. 890,377, filed of even date herewith and assigned to the same assignee as the present application. A focusing lens may also be advantageously used in conjunction with the transducer.

Further features and advantages of the invention will become more readily apparent from the following detailed description when taken in conjunction with the accompanying drawings.

DESCRIPTION OF THE PREFERRED EMBODIMENT

Figure 1:
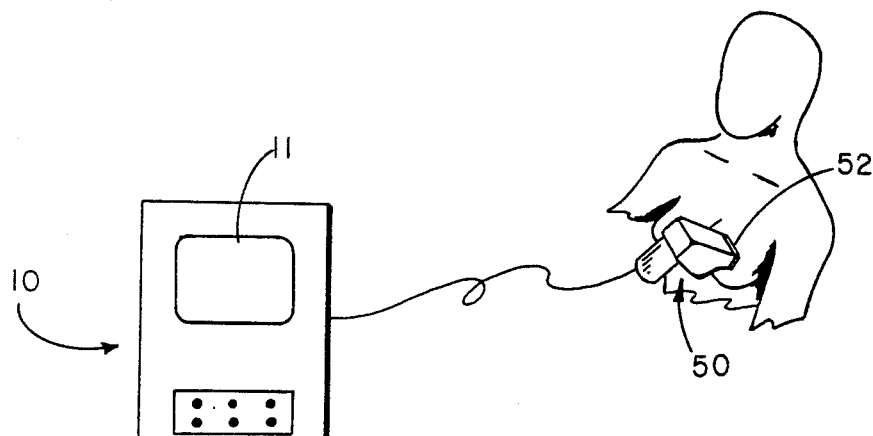
FIG. 1 illustrates the operation of a scanning apparatus which employs the improvements of the invention.
Figure 2:
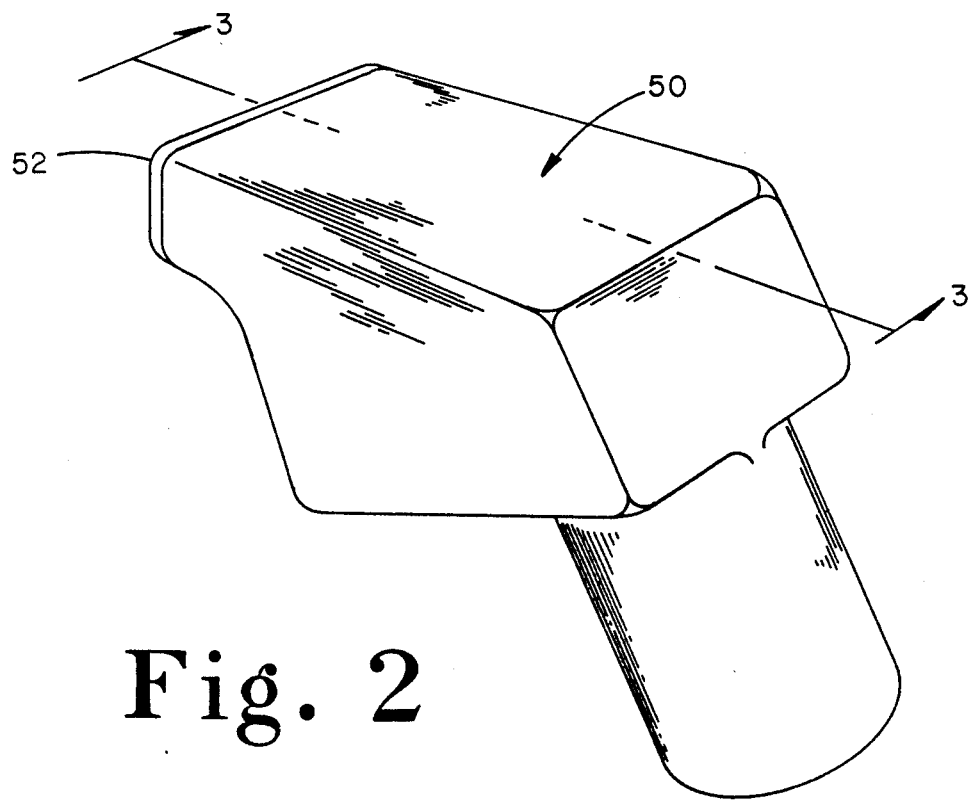
FIG. 2 is an elevational perspective view of an embodiment of the scanning module of the FIG. 1 apparatus.

Referring to FIG. 1, there is shown an illustration of a scanning apparatus which employs the improvements of the invention. A console 10 is provided with a display 11 which may typically be a cathode ray tube television-type display, and a suitable control panel. A video tape recorder or suitable photographic means may also be included in the console. The console will also typically house power supplies and portions of the timing and processing circuitry of the system, to be described. A portable scanning module or probe 50 (shown in FIG. 2) is coupled to the console by cable 48. The scanning module has a window 52 at one end thereof through which an investigating ultrasound beam is emitted and a reflected beam is received. During operation of the apparatus, the scanning module 50 is hand held to position the window 52 over a part of the body to be imaged. For example, in FIG. 1 the scanning module is positioned such that a cross-section through a breast will be obtained. Imaging of other sections through the breast or other portions of the body is readily attained by moving the probe to the desired position and orientation, the relative orientation of the scanning window determining the angle of the cross-section taken.

Figure 3:
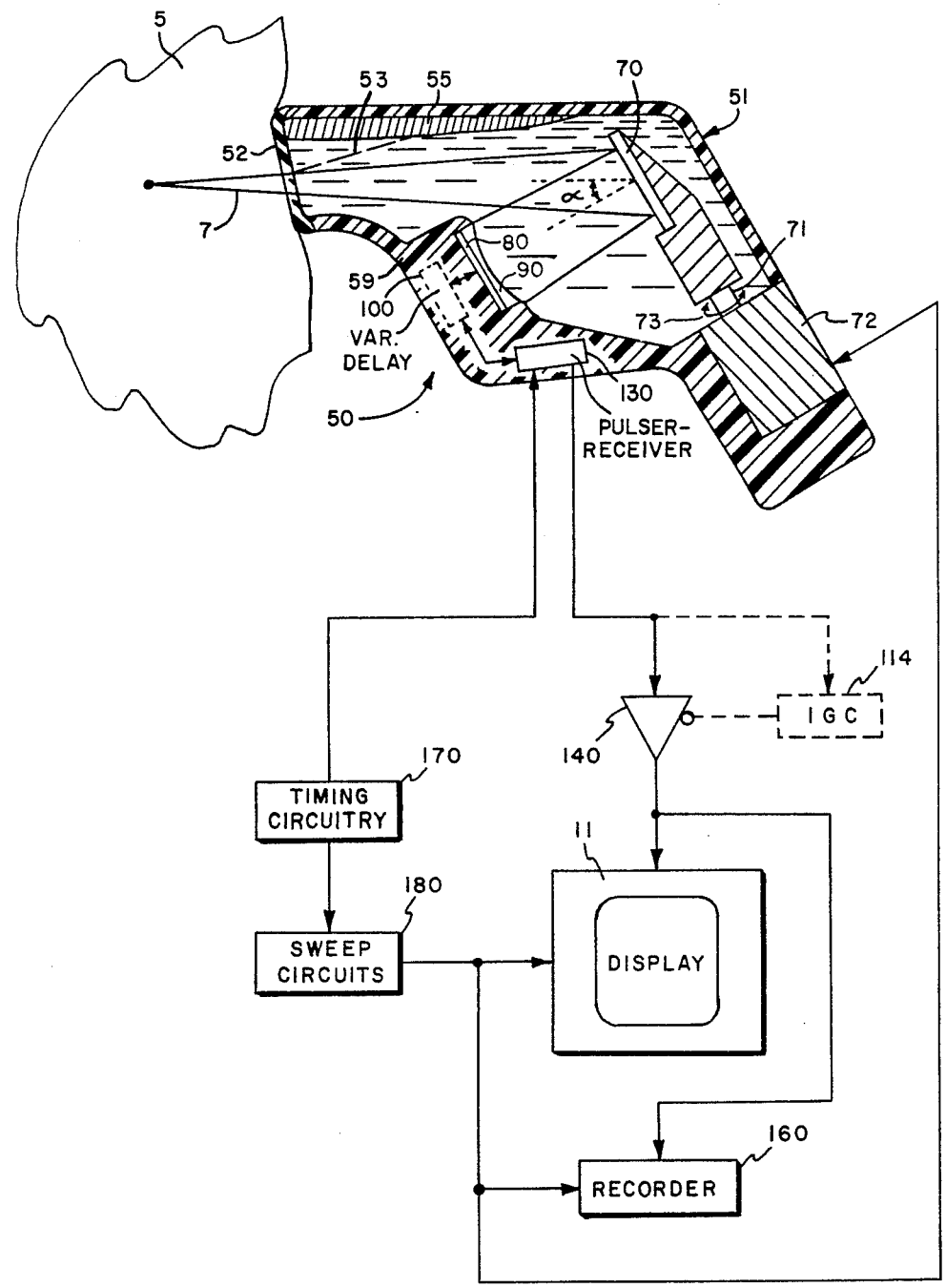
FIG. 3 shows a cross-sectional view of the scanning module of FIG. 2 as taken through a section defined by arrows 3—3, along with diagrams of portions of circuitry therein and in the accompanying console.

Referring to FIG. 3, there is shown a cross-sectional view of a portion of the scanning module or probe 50 along with diagrams of portions of the circuitry therein and in console 10 used in conjunction therewith. A fluid-tight enclosure 51, which may be formed of a sturdy plastic, has scanning window 52 at the front end thereof. The enclosure 51 is filled with a suitable fluid 57, for example water. In the present embodiment the scanning window 52 is relatively flat and may be formed of any suitable material, for example methyl methacrylate or nylon. A reflective scanner 70, which is flat in the present embodiment but which may be curved to provide focusing if desired, is positioned at the approximate rear of the enclosure 51 and substantially faces the window 52. The scanner 70 is mounted on a shaft 71 which passes through a suitable seal and is connected to an electric motor 72 which is mounted in a recess in enclosure 51 and is driven to provide the desired oscillatory motion of scanner 70, as depicted by curved two-headed arrow 73.

An ultrasonic transducer 80 is mounted in a compartment 59 of enclosure 51, the transducer being mounted relatively frontwardly of reflective scanner 70 in the module 50 with the ultrasound-emitting face of the transducer generally facing rearwardly in the module 50 and being directed toward the reflective scanner 70. The transducer 80 is positioned such that the ultrasound beam which it emits is reflected by the scanner 70 to double back past transducer 80 before passing through the window 52. In particular, the transducer 80 is positioned such that the ultrasound beam emitted therefrom and reflected toward the window 52 (or conversely the beam reflected by the body 5 being investigated back through the window 52 and to the transducer 80) subtends at an angle at the reflective scanner of less than about forty-five degrees. Preferably, this angle, which is represented in FIG. 3 by the angle α of the central ray of an ultrasound beam 7, subtends an angle at the reflector 70 of about thirty degrees. The scanner 70 preferably has a reflective surface formed of a material which results in a relatively small critical angle so that the beam impinging almost directly on the reflector surface will not pass through the reflector. A sapphire surface on the reflector 70, disposed in water 57, has a critical angle of about fourteen degrees (as determined by the relative indices of refraction of ultrasound as between sapphire and water), so the relative positions and orientations of the transducer, reflector, and window in the scanning module 50 are selected to insure that the beam impinging upon the reflector 70 from either direction will be at an angle which exceeds the critical angle. It is seen that this arrangement makes particularly efficient use of the volume of fluid 57 in the module 50 since the beam 7 is effectively "doubling back" past the transducer and experiencing a relatively large travel distance through a relatively small volume of water. A beryllium surface also results in a small critical angle, but its toxicity renders it less desirable to work with. A further alternative is to employ a reflective scanner having a trapped gas layer, as disclosed in copending U.S. Application Ser. No. 665,898, assigned to the same assignee of the present application. As described therein, the liquid/gas interface at the reflector surface insures total reflection regardless of the beam arrival angle.

A pulser/receiver circuit 130 alternately provides energizing pulses to and receives echo signals from the transducer 80. As used herein, the term pulser/receiver is intended to include any combined or separate circuits for producing the energizing signals for the transducer and receiving echo signals therefrom. If dynamic focusing is employed, the transducer 80 may be segmented and the pulser/receiver circuitry 130 may be coupled to the segments of transducer 80 via variable delay circuitry 100, shown in dashed line. The pulser/receiver circuitry 130 and the variable delay circuitry 100 (if present) are typically, although not necessarily, located in the scanning module 50, for example within the compartment 59. The receiver portion of circuit 130 is coupled through an amplifier 140 to display 11 and to recorder 160, which may be any suitable recording, memory, and/or photographic means, for example a video tape recorder. If desired, gain control circuitry including an interactive gain compensation ("IGC") capability, as represented by the block 141 (shown in dashed line), can be employed. Interactive gain compensation techniques are described in detail in the U.S. Pat. No. 4,043,181, assigned to the same assignee as the present application. This circuitry compensates the amplitude of later arriving signals for attenuation experienced during passage through body tissue and losses due to prior reflections. Accordingly, if an IGC capability is employed, the amplifier 140 may be used as a gain control amplifier under control of an IGC signal from circuit 141. Timing circuitry 170 generates timing signals which synchronize operation of the system, the timing signals being coupled to pulser/receiver 130 and also to sweep circuitry 180 which generates the signals that control the oscillations of scanner 70 and the vertical and horizontal sync signals for the display 11 and recorder 160. If dynamic focusing is employed, as described in copending U.S. patent application Ser. No. 665,898, assigned to the same assignee as the present application, the timing signals may also be coupled to phase control circuitry (not shown) which produces signals that control the variation of the delays in variable delay circuit 100. Also, a lens 90, which typically has a relatively flat surface bonded to the transducer and a curved concave surface which provides focusing, may be employed in the scanning module 50. The lens may be formed of a plastic material with the material being selected in accordance with the principle set forth in U.S. Pat. No. 3,958,559, assigned to the same assignee as the present application. As disclosed in that patent, by selecting the lens material in accordance with specified parameters, "apodization" is achieved; i.e., undesired side lobes, caused by factors such as finite transducer size, are minimized. Further, as disclosed in the referenced patent, the lens may have a generally elliptical contour to attain advantageous focusing characteristics. If desired, however, alternative means of focusing can be employed, such as electronic focusing using a segmented transducer, or providing curvature in the transducer or reflector surface.

Operation of the system is as follows: Upon command from the timing circuits to the pulser in circuitry 130 generates pulses which excite the transducer 80, the segments of transducer 80 being excited via variable delay circuitry 100, under control of phase control circuitry, when dynamic focusing is employed. (As is known in the art, the depth of focus can be varied electronically in a dynamically focused system by imparting predetermined delays or phase changes to different segments of the transducer 80. In such case the ultrasound pulse is typically launched with the variable delay circuitry set so that the transmitted beam is focused at a point which is between the center of the field and the deepest point within the body at which an image is being sought.) The beam of ultrasound resulting from pulsing the transducer is reflected by reflector 70 through the window 52 and into the body 5. The timing circuitry now causes the pulser/receiver 130 to switch into a "receive" or "listen" mode. (If dynamic focusing is employed, a cycle of the phase control circuitry would be activated.) Now, as the ultrasound echoes are received from the body via window 52 and reflected off scanner 70 toward transducer 80, the transducer serves to convert the received ultrasound energy into electrical signals. (Again, for a dynamic focusing implementation, the transducer segments serve to convert the received ultrasonic energy into electrical signals which are combined in proper phase relationship for focusing on particular reflection origination points in the range of depths being investigated.) For a two-dimensional "B-scan" display, a sweep over the range of depth corresponds to a horizontal scanline of the display, so the timing signals from circuitry 170 synchronize the horizontal sync of the display such that the active portion of one scanline of the display corresponds to the time of arrival of echoes from a given range within the body 5, typically from the patient's skin up to a fixed preselected depth in the body. The second dimension of the desired cross-sectional image is attained by the slower mechanical scan of reflective scanner 70 which is synchronized with the vertical sweep rate of the display and recorder by the sweep circuitry 180. The received signals are coupled through amplifier 140 to display 11 wherein the received signals modulate the brightness of the scanning raster to obtain the desired cross-sectional image, with each scanline of the display representing a depth echo profile of the body for a particular angular orientation of the scanner 70. The received signals are also recorded on the video tape recorder 160.

Figure 4:
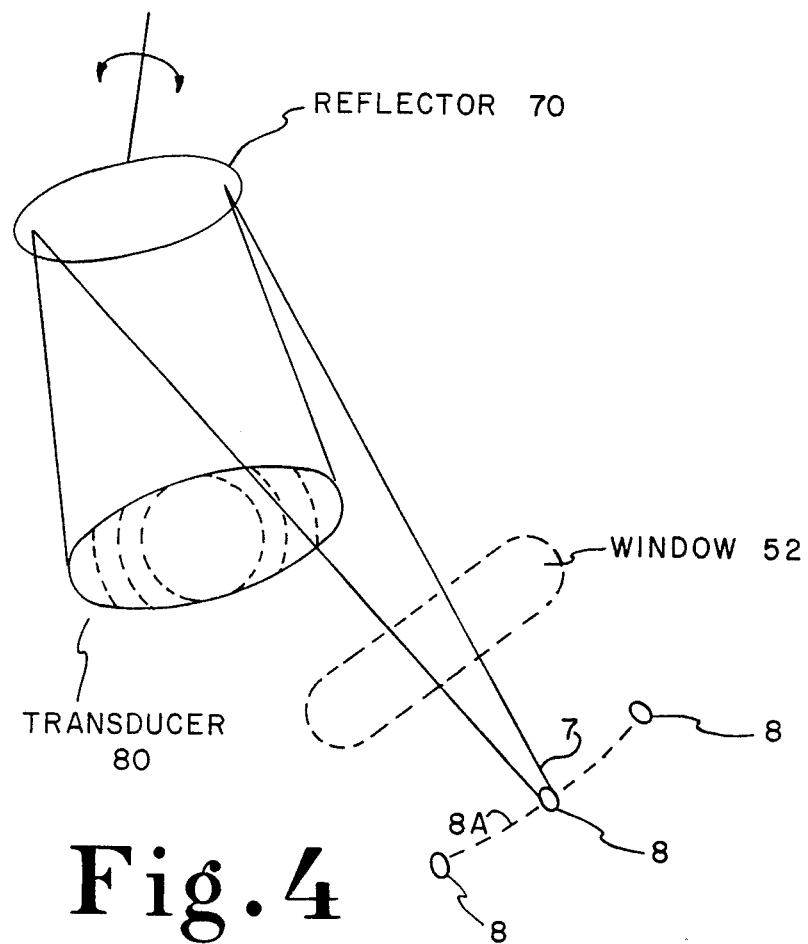
FIG. 4 illustrates the scan of the beam from the transducer and reflector of the scanning module of FIG. 2.
Figure 5:
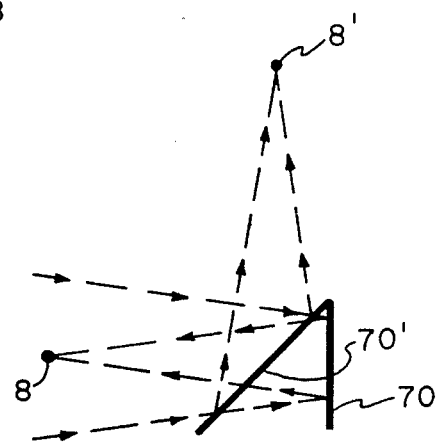
FIG. 5 is a simplified diagram which illustrates how the configuration of the disclosed embodiment permits use of a shorter reflective scanner.

FIG. 4 illustrates the nature of the scan of beam 7, indicated by the motion of the scanning spot 8 along dashed line 8A. As disclosed in my above-referenced copending U.S. Application Ser. No. 890,377, and illustrated in FIG. 4, the transducer 80 preferably has a generally elliptical shape and is elongated along the direction of scan. (The dashed lines on the transducer 40 represent its segmentation in the event dynamic focusing is employed.) After focusing, such as by lens 90 (FIG. 3), which is bonded to transducer 80 and preferably conforms circumferentially in shape thereto, the resultant spot 8 is elongated in a direction normal to the direction of scan. The thickness of the investigated "slice" is therefore substantially larger (preferably at least twice as large) as a resolution element in the direction of scan. The reflector 70 can also be of elongated generally elliptical shape, as shown in FIG. 4. The torque required to drive the reflector is strongly dependent upon its size and mass. The generally elliptical shape of the mirror is advantageous in that it requires less power to drive as compared to a larger more symmetrical mirror. Also, the "folded back" configuration allows use of a mirror having a reduced size as compared, for example, to a system wherein the beam is reflected at about a right angle. This results in an even further reduction in required drive power. The simplified diagram of FIG. 5 illustrates the principle. It is seen geometrically that the reflector 70' (which deflects the incident beam at a right angle to focus 8') is necessarily longer by a factor of $\sqrt{2}$ than the reflector 70 which reflects the beam directly back toward focus 8.

In accordance with a feature disclosed in my above-referenced copending U.S. Application Ser. No. 890,377, the window 52 is inclined at an angle, for example an angle of the order of 10°, with respect to the normal to the ultrasound incident thereon (see FIG. 3). This incline tends to cause any ultrasound that is undesirably reflected from the window (which may be formed of a relatively rigid material) to miss the transducer. An absorbing medium 55, which may, for example, by syntactic foam, is disposed in the path of internally reflected ultrasound, represented in FIG. 3 by the dotted line 53. In the illustrated embodiment the window is inclined toward the top of module 50 and the absorbing medium 55 is disposed on the top inner surface of enclosure 51.

The invention has been described with reference to particular embodiments, but variations within the spirit and scope of the invention will occur to those skilled in the art. For example, some of the circuitry of the console may be housed in the scanning module, if desired, or vice versa, the basic consideration being the desire to maintain portability of the module while still minimizing the noise-susceptibility of low-level signals passing through cables between the scanning module and the console.

I claim:

1. In an apparatus for ultrasonically imaging sections of a body by transmitting ultrasonic energy in to the body and determining the characteristics of the ultrasonic energy reflected therefrom, said apparatus including timing means for generating timing signals; energizing/receiving means alternately operative in response to timing signals; and display/record means synchronized with said timing signals for displaying and/or recording image-representative signals from the energizing/receiving means; an improved portable scanning module, comprising:

a fluid-tight enclosure having a window and a reflective scanner spaced from the window and generally facing the window;
   a transducer for converting energy from said energizing/receiving means to a beam of ultrasonic energy and for converting reflected ultrasonic energy to electrical signals, said transducer being stationarily mounted in said enclosure with the ultrasound-emitting face of the transducer generally facing said reflective scanner;
   said reflective scanner being pivotally mounted to scan said beam across said window in a scan path that maintains substantially constant, at a non-zero angle of less than about forty-five degrees, the angle formed between the central ray of said beam incident on said reflective scanner and the plane defined by the path of the central ray reflected from said reflective scanner during the scan;
   fluid means contained in said enclosure; and
   driving means synchronized with said timing signals for moving said scanner in periodic fashion.

2. The scanning module as defined by claim 1 wherein said angle is about thirty degrees.

3. The scanning module as defined by claim 2 wherein the reflective surface of said reflective scanner includes a layer of sapphire material.

4. The scanning module as defined by claim 2 wherein said transducer is elongated along the direction of scanning of said beam.

5. The scanning module as defined by claim 1 wherein the reflective surface of said reflective scanner includes a layer of sapphire material.

6. The scanning module as defined by claim 5 further comprising a focusing lens coupled to said transducer.

7. The scanning module as defined by claim 5 wherein said transducer is elongated along the direction of scanning of said beam.

8. The scanning module as defined by claim 7 wherein said window is elongated along the direction of scanning of said beam.

9. The scanning module as defined by claim 8 wherein said window is inclined at an angle with respect to the normal to the ultrasound beam incident on said window.

10. The scanning module as defined by claim 1 wherein the reflective surface of said reflective scanner includes a layer of beryllium.

11. The scanning module as defined by claim 1 further comprising a focusing lens coupled to said transducer.

12. The scanning module as defined by claim 11 wherein said transducer is elongated along the direction of scanning of said beam.

13. Apparatus as defined by claim 12 wherein said reflective scanner is elongated in the direction of elongation of the ultrasound beam incident thereon.

14. Apparatus as defined by claim 13 wherein said reflective scanner is pivotally mounted in said fluid means on an axis perpendicular to its length, and wherein said driving means is operative to oscillate said reflective scanner.

15. The scanning module as defined by claim 1 wherein said transducer is elongated along the direction of scanning of said beam.

16. The scanning module as defined by claim 15 wherein said window is elongated along the direction of scanning of said beam.

17. The scanning module as defined by claim 16 wherein said window is inclined at an angle with respect to the normal to the ultrasound beam incident on said window.

18. The scanning module as defined by claim 1 wherein said window is inclined at an angle with respect to the normal to the ultrasound beam incident on said window.

19. Apparatus for ultrasonically imaging sections of a body by transmitting ultrasonic energy into the body and determining the characteristics of the ultrasonic energy reflected therefrom, comprising:
   timing means for generating timing signals;
   energizing/receiving means alternately operative in response to timing signals;
   display/record means synchronized with said timing signals for displaying and/or recording image-representative signals from the energizing/receiving means; and
   a portable scanning module which includes:
      a fluid-tight enclosure having a window and a reflective scanner spaced from the window and facing the window;
      a transducer for converting energy from said energizing/receiving means to a beam of ultrasonic energy and for converting reflected ultrasonic energy to electrical signals, said transducer being stationarily mounted in said enclosure with the ultrasound-emitting face of the transducer generally facing said reflective scanner;
      said reflective scanner being pivotally mounted to scan said beam across said window in a scan path that maintains substantially constant, at a non-zero angle of less than about forty-five degrees, the angle formed between the central ray of said beam incident on said reflective scanner and the plane defined by the path of the central ray reflected from said reflective scanner during the scan;
      fluid means contained in said enclosure; and
      driving means synchronized with said timing signals for moving said scanner in periodic fashion.

20. Apparatus as defined by claim 19 wherein said angle is about thirty degrees.

21. Apparatus as defined by claim 20 wherein the reflective surface of said reflective scanner includes a layer of sapphire material.

22. Apparatus as defined by claim 20 wherein said transducer is elongated along the direction of scanning of said beam.

23. Apparatus as defined by claim 19 wherein the reflective surface of said reflective scanner includes a layer of sapphire material.

24. Apparatus as defined by claim 23 further comprising a focusing lens coupled to said transducer.

25. Apparatus as defined by claim 24 wherein said transducer is elongated along the direction of scanning of said beam.

26. Apparatus as defined by claim 23 wherein said transducer is elongated along the direction of scanning of said beam.

27. Apparatus as defined by claim 26 wherein said window is elongated along the direction of scanning of said beam.

28. Apparatus as defined by claim 27 wherein said window is inclined at an angle with respect to the normal to the ultrasound beam incident on said window.

29. Apparatus as defined by claim 19 wherein the reflective surface of said reflective scanner includes a layer of beryllium.

30. Apparatus as defined by claim 19 further comprising a focusing lens coupled to said transducer.

31. Apparatus as defined by claim 19 wherein said transducer is elongated along the direction of scanning of said beam.

32. Apparatus as defined by claim 31 wherein said window is elongated along the direction of scanning of said beam.

33. Apparatus as defined by claim 32 wherein said window is inclined at an angle with respect to the normal to the ultrasound beam incident on said window.

34. Apparatus as defined by claim 19 wherein said window is inclined at an angle with respect to the normal to the ultrasound beam incident on said window.

35. In an apparatus for ultrasonically imaging sections of a body by transmitting ultrasonic energy into the body and determining the characteristics of the ultrasonic energy reflected therefrom, said apparatus including timing means for generating timing signals; energizing/receiving means alternately operative in response to timing signals; and display/record means synchronized with said timing signals for displaying and/or recording image-representative signals from the energizing/receiving means; an improved portable scanning module, comprising:
   a fluid-tight enclosure having a window at about the front thereof and a reflective scanner at about the rear thereof and generally facing the window;
   a transducer for converting energy from said energizing/receiving means to a beam of ultrasonic energy and for converting reflected ultrasonic energy to electrical signals, said transducer being stationarily mounted in said enclosure frontwardly of said reflective scanner with the ultrasound-emitting face of said transducer facing said reflective scanner such that the entire ultrasound beam emitted by said transducer and reflected by said reflective scanner doubles back past the plane of said face of said transducer before passing through said window;

said reflective scanner being pivotally mounted to scan said beam across said window in a scan path that maintains substantially constant, at a non-zero angle, the angle formed between the central ray of said beam incident on said reflective scanner and the plane defined by the path of the central ray reflected from said reflective scanner during the scan;

fluid means contained in said enclosure; and driving means synchronized with said timing signals for moving said scanner in periodic fashion.

36. The scanning module as defined by claim 35 wherein the reflective surface of said reflective scanner includes a layer of sapphire material.

37. The scanning module as defined by claim 36 further comprising a focusing lens coupled to said transducer.

38. The scanning module as defined by claim 37 wherein said transducer is elongated along the direction of scanning of said beam.

39. The scanning module as defined by claim 38 wherein said window is elongated along the direction of scanning of said beam.

40. The scanning module as defined by claim 36 wherein said transducer is elongated along the direction of scanning of said beam.

41. The scanning module as defined by claim 39 wherein said window is inclined at an angle with respect to the normal to the ultrasound beam incident on said window.

42. The scanning module as defined by claim 35 further comprising a focusing lens coupled to said transducer.

43. The scanning module as defined by claim 33 wherein said transducer is elongated along the direction of scanning of said beam.

44. The scanning module as defined by claim 43 wherein said window is elongated along the direction of scanning of said beam.

45. The scanning module as defined by claim 44 wherein said window is inclined at an angle with respect to the normal to the ultrasound beam incident on said window.

46. Apparatus as defined by claim 43 wherein said reflective scanner is elongated in the direction of elongation of the ultrasound beam incident thereon.

47. Apparatus as defined by claim 46 wherein said reflective scanner is pivotally mounted in said fluid means on an axis perpendicular to its length, and wherein said driving means is operative to oscillate said reflective scanner.

48. The scanning module as defined by claim 35 wherein said window is inclined at an angle with respect to the normal to the ultrasound beam incident on said window.

49. Apparatus for ultrasonically imaging sections of a body by transmitting ultrasonic energy into the body and determining the characteristics of the ultrasonic energy reflected therefrom, comprising:

timing means for generating timing signals;

energizing/receiving means alternately operative in response to timing signals;

display/record means synchronized with said timing signals for displaying and/or recording image-representative signals from the energizing/receiving means; and a portable scanning module which includes:

a fluid-tight enclosure having a window at about the front thereof and a reflective scanner spaced from the window and generally facing the window;

a transducer for converting energy from said energizing/receiving means to a beam of ultrasonic energy and for converting reflected ultrasonic energy to electrical signals, said transducer being stationarily mounted in said enclosure frontwardly of said reflective scanner with the ultrasound-emitting face of said transducer facing said reflective scanner such that the entire ultrasound beam emitted by said transducer and reflected by said reflective scanner doubles back past the plane of said face of said transducer before passing through said window;

said reflective scanner being pivotally mounted to scan said beam across said window in a scan path that maintains substantially constant, at a non-zero angle, the angle formed between the central ray of said beam incident on said reflective scanner and the plane defined by the path of the central ray reflected from said reflective scanner during the scan;

fluid means contained in said enclosure; and driving means synchronized with said timing signals for moving said scanner in periodic fashion.

50. Apparatus as defined by claim 49 wherein the reflective surface of said reflective scanner includes a layer of sapphire material.

51. Apparatus as defined by claim 50 further comprising a focusing lens coupled to said transducer.

52. Apparatus as defined by claim 51 wherein said transducer is elongated along the direction of scanning of said beam.

53. Apparatus as defined by claim 52 wherein said window is elongated along the direction of scanning of said beam.

54. Apparatus as defined by claim 53 wherein said window is inclined at an angle with respect to the normal to the ultrasound beam incident on said window.

55. Apparatus as defined by claim 50 wherein said transducer is elongated along the direction of scanning of said beam.

56. Apparatus as defined by claim 49 further comprising a focusing lens coupled to said transducer.

57. Apparatus as defined by claim 49 wherein said transducer is elongated along the direction of scanning of said beam.

58. Apparatus as defined by claim 57 wherein said window is elongated along the direction of scanning of said beam.

59. Apparatus as defined by claim 58 wherein said window is inclined at an angle with respect to the normal to the ultrasound beam incident on said window.

60. Apparatus as defined by claim 49 wherein said window is inclined at an angle with respect to the normal to the ultrasound beam incident on said window.

61. In an apparatus for ultrasonically imaging sections of a body by transmitting ultrasonic energy into the body and determining the characteristics of the ultrasonic energy reflected therefrom, said apparatus including timing means for generating timing signals; energizing/receiving means alternately operative in response to timing signals; and display/record means synchronized with said timing signals for displaying and/or recording image-representative signals from the energizing/receiving means; an improved portable scanning module, comprising:

a fluid-tight enclosure having a window and a reflective scanner spaced from the window and generally facing the window, the reflective surface of said scanner including a layer of sapphire material;

a transducer for converting energy from said energizing/receiving means to a beam of ultrasonic energy and for converting reflected ultrasonic energy to electrical signals, said transducer being mounted in said enclosure with the ultrasound-emitting face of the transducer generally facing said reflective scanner and being positioned with respect to said reflective scanner such that an ultrasound beam reflected by said reflective scanner as between said transducer and said window subtends an angle at said reflective scanner of less than about forty-five degrees;

fluid means contained in said enclosure; and driving means synchronized with said timing signals for moving said scanner in periodic fashion.

62. The scanning module as defined by claim 61 wherein said angle is about thirty degrees.

63. The scanning module as defined by claim 61 further comprising a focusing lens coupled to said transducer.

64. The scanning module as defined by claim 61 wherein said transducer is elongated along the direction of scanning of said beam.

65. The scanning module as defined by claim 64 wherein said window is elongated along the direction of scanning of said beam.

66. The scanning module as defined by claim 65 wherein said window is inclined at an angle with respect to the normal to the ultrasound beam incident on said window.

67. Apparatus as defined by claim 64 wherein said reflective scanner is elongated in the direction of elongation of the ultrasound beam incident thereon.

68. Apparatus as defined by claim 67 wherein said reflective scanner is pivotally mounted in said fluid means on an axis perpendicular to its length, and wherein said driving means is operative to oscillate said reflective scanner.

69. In an apparatus for ultrasonically imaging sections of a body of transmitting ultrasonic energy into the body and determining the characteristics of the ultrasonic energy reflected therefrom, said apparatus including timing means for generating timing signals; energizing/receiving means alternately operative in response to timing signals; and display/record means synchronized with said timing signals for displaying and/or recording image-representative signals from the energizing/receiving means; an improved portable scanning module, comprising:

a fluid-tight enclosure having a window and a reflective scanner spaced from the window and generally facing the window, the reflective surface of said scanner including a layer of beryllium;

a transducer for converting energy from said energizing/receiving means to a beam of ultrasonic energy and for converting reflected ultrasonic energy to electrical signals, said transducer being mounted in said enclosure with the ultrasound-emitting face of the transducer generally facing said reflective scanner and being positioned with respect to said reflective scanner such that an ultrasound beam reflected by said reflective scanner as between said transducer and said window subtends an angle at said reflective scanner of less than about forty-five degrees;

fluid means contained in said enclosure; and driving means synchronized with said timing signals for moving said scanner in periodic fashion.

70. Apparatus for ultrasonically imaging sections of a body for transmitting ultrasonic energy into the body and determining the characteristics of the ultrasonic energy reflected therefrom, comprising:

timing means for generating timing signals;

energizing/receiving means alternately operative in response to timing signals, display/record means synchronized with said timing signals for displaying and/or recording image-representative signals from the energizing/receiving means; and a portable scanning module which includes:

a fluid-tight enclosure having a window and a reflective scanner spaced from the window and generally facing the window, the reflective surface of said scanner including a layer of sapphire material;

a transducer for converting energy from said energizing/receiving means to a beam of ultrasonic energy and for converting reflected ultrasonic energy to electrical signals, said transducer being mounted in said enclosure with the ultrasound-emitting face of the transducer generally facing said reflective scanner and being positioned with respect to said reflective scanner such that an ultrasound beam reflected by said reflective scanner as between said transducer and said window subttends an angle at said reflective scanner of less than about forty-five degrees;

fluid means contained in said enclosure; and driving means synchronized with said timing signals for moving said scanner in periodic fashion.

71. Apparatus as defined by claim 70 wherein said angle is about thirty degrees.

72. Apparatus as defined by claim 70 further comprising a focusing lens coupled to said transducer.

73. Apparatus as defined by claim 70 wherein said transducer is elongated along the direction of scanning of said beam.

74. Apparatus as defined by claim 73 wherein said window is elongated along the direction of scanning of said beam.

75. Apparatus as defined by claim 74 wherein said window is inclined at an angle with respect to the normal to the ultrasound beam incident on said window.

76. Apparatus for ultrasonically imaging sections of a body by transmitting ultrasonic energy into the body and determining the characteristics of the ultrasonic energy reflected therefrom, comprising:

timing means for generating timing signals;

energizing/receiving means alternately operative in response to timing signals;

display/record means synchronized with said timing signals for displaying and/or recording image-representative signals from the energizing/receiving means; and a portable scanning module which includes:
- a fluid-tight enclosure having a window and a reflective scanner spaced from the window and generally facing the window, the reflective surface of said scanner including a layer of sapphire material;
- a transducer for converting energy from said energizing/receiving means to a beam of ultrasonic energy and for converting reflected ultrasonic energy to electrical signals, said transducer being mounted in said enclosure with the ultrasound-emitting face of the transducer generally facing said reflective scanner and being positioned with respect to said reflective scanner such that an ultrasound beam reflected by said reflective scanner as between said transducer and said window subtends an angle at said reflective scanner of less than about forty-five degrees;
- fluid means contained in said enclosure; and
- driving means synchronized with said timing signals for moving said scanner in periodic fashion.

77. Apparatus for ultrasonically imaging sections of a body by transmitting ultrasonic energy into the body and determining the characteristics of the ultrasonic energy reflected therefrom, comprising:
- timing means for generating timing signals;
- energizing/receiving means alternately operative in response to timing signals;
- display/record means synchronized with said timing signals for displaying and/or recording image-representative signals from the energizing/receiving means; and
- a portable scanning module which includes:
  - a fluid-tight enclosure having a window at about the front thereof and a reflective scanner spaced from the window and generally facing the window, the reflective surface of said scanner including a layer of sapphire material;
  - a transducer for converting energy from said energizing/receiving means to a beam of ultrasonic energy and for converting reflected ultrasonic energy to electrical signals, said transducer being mounted in said enclosure frontwardly of said reflective scanner with the ultrasound-emitting face of said transducer generally facing said reflective scanner such that an ultrasound beam emitted by said transducer and reflected by said reflective scanner doubles back past said transducer before passing through said window;
  - fluid means contained in said enclosure; and
  - driving means synchronized with said timing signals for moving said scanner in periodic fashion.

78. Apparatus as defined by claim 77 further comprising a focusing lens coupled to said transducer.

79. Apparatus as defined by claim 78 wherein said transducer is elongated along the direction of scanning of said beam.

80. Apparatus as defined by claim 79 wherein said window is elongated along the direction of scanning of said beam.

81. Apparatus as defined by claim 80 wherein said window is inclined at an angle with respect to the normal to the ultrasound beam incident on said window.

82. Apparatus as defined by claim 77 wherein said transducer is elongated along the direction of scanning of said beam.

83. In an apparatus for ultrasonically imaging sections of a body by transmitting ultrasonic energy into the body and determining the characteristics of the ultrasonic energy reflected therefrom, said apparatus including timing means for generating timing signals; energizing/receiving means alternately operative in response to timing signals; and display/record means synchronized with said timing signals for displaying and/or recording image-representative signals from the energizing/receiving means; an improved portable scanning module, comprising:
- a fluid-tight enclosure having a window at about the front thereof and a reflective scanner at about the rear thereof and generally facing the window, the reflective surface of said scanner including a layer of sapphire material;
- a transducer for converting energy from said energizing/receiving means to a beam of ultrasonic energy and for converting reflected ultrasonic energy to electrical signals, said transducer being mounted in said enclosure frontwardly of said reflective scanner with the ultrasound-emitting face of said transducer generally facing said reflective scanner such that the ultrasound beam emitted by said transducer and reflected by said reflective scanner doubles back past said transducer before passing through said window;
- fluid means contained in said enclosure; and
- driving means synchronized with said timing signals for moving said scanner in periodic fashion.

84. The scanning module as defined by claim 83 further comprising a focusing lens coupled to said transducer.

85. The scanning module as defined by claim 84 wherein said transducer is elongated along the direction of scanning of said beam.

86. The scanning module as defined by claim 85 wherein said window is elongated along the direction of scanning of said beam.

87. The scanning module as defined by claim 86 wherein said window is inclined at an angle with respect to the normal to the ultrasound beam incident on said window.

88. Apparatus as defined by claim 85 wherein said reflective scanner is elongated in the direction of elongation of the ultrasound beam incident thereon.

89. Apparatus as defined by claim 88 wherein said reflective scanner is pivotally mounted in said fluid means on an axis perpendicular to its length, and wherein said driving means is operative to oscillate said reflective scanner.

90. The scanning module as defined by claim 83 wherein said transducer is elongated along the direction of scanning of said beam.

* * * * *